United States Patent [19]

Kleber et al.

[11] 4,197,350
[45] Apr. 8, 1980

[54] QUATERNIZED AMINE-AMIDE CONDENSATION PRODUCTS AND THEIR USE IN OIL-CONTAINING FIBER PREPARATIONS

[75] Inventors: Rolf Kleber, Neu-Isenburg; Wolfgang Wagemann, Hofheim am Taunus, both of Fed. Rep. of Germany

[73] Assignee: Hoechst Aktiengesellschaft, Frankfurt am Main, Fed. Rep. of Germany

[21] Appl. No.: 952,700

[22] Filed: Oct. 19, 1978

[30] Foreign Application Priority Data

Oct. 25, 1977 [DE] Fed. Rep. of Germany ....... 2747723

[51] Int. Cl.² .......................... C07F 9/02; D02G 3/00
[52] U.S. Cl. ...................................... 428/392; 252/8.8; 260/925; 260/987; 428/393; 428/394; 428/395
[58] Field of Search .............. 260/925, 443, 987, 403; 252/8.8; 428/375, 392, 393, 394, 395

[56] References Cited

U.S. PATENT DOCUMENTS 3,634,117  1/1972  Wegerhoff ...................... 260/925 X

FOREIGN PATENT DOCUMENTS 45-573  9/1970  Japan ...................................... 260/403
28885  9/1970  Japan ...................................... 260/403

*Primary Examiner*—Lorraine T. Kendell
*Attorney, Agent, or Firm*—Connolly and Hutz

[57] ABSTRACT

Quaternized amine-amide condensation products which are obtained by condensation of an amine of the formula $$R_1R_2N-(CH_2)_n-NH_2$$

with a lower alkanecarboxylic acid, and subsequent quaternization with a trialkyl phosphate. These products are suitable as fiber preparation agents.

3 Claims, No Drawings

QUATERNIZED AMINE-AMIDE CONDENSATION PRODUCTS AND THEIR USE IN OIL-CONTAINING FIBER PREPARATIONS

It is generally necessary to add antistatic compounds to fiber preparation agents in order to obtain optimum smoothness of the finished fibers. As antistatic agents for preparations, especially filament preparations, there are used a number of chemically different products, which are the following, according to Rath, Lehrbuch der Textilchemie, p. 342: Anionic and cationic products, to a certain extent also nonionic polyethylene oxides and the adducts thereof. Rath (loc.cit., p. 792) gives also a classification, according to which phosphoric acid esters, quaternary ammonium compounds, fatty acid-imidazoline derivatives etc. are used as antistatic agents in fiber preparations.

A problem of filament preparations resides in the fact that in these concentrates generally formed on the basis of mineral oils or ester oils the above antistatic agents are scarcely soluble. Several fiber preparation manufactures try to elude this problem by using as antistatic agents for example phosphoric acid esters neutralized by organic bases and thus being oil-soluble to a certain extent. Thus, U.S. Pat. No. 2,742,379 proposes alkanolamine salts of alkyl phosphates as antistatic agents; in Example I, for example, the diethanolamine salt of a $P_2O_5$ ester of dodecanol.

Although these products are oil-soluble to a certain extent, the thermostability of the alkanolamine salts is poor, so that, when operating with these phosphate ester salts in the industrial practice, yellow discoloration of the fibers occurs very often after fixation and texturing. On the other hand, quaternary ammonium compounds are very efficient antistatic agents. These products, however, are not appreciated in oil-containing filament preparations, because, due to their high polarity giving the excellent antistatic effect in the practice, they are generally insoluble in the oil-containing concentrates, and because they, too, tend to yellowing at elevated temperatures.

It has now been found that oil-containing fiber preparations having a content of quaternary ammonium compounds can be prepared when quaternized amine-amide condensation products are used as quaternary ammonium compounds.

Subject of this invention are therefore quaternized amine-amide condensation products obtained by condensation of an amine of the formula

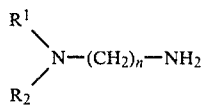

with a carboxylic acid of the formula $R_4$—COOH and subsequent quaternization with a trialkyl phosphate of the formula

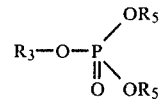

in which formulae
$R_1$ is an alkyl or alkenyl group having from 7 to 20 carbon atoms,
$R_2$ is an alkyl group having from 1 to 20 carbon atoms, or a hydrogen atom,
$R_3$ and $R_5$ are identical or different alkyl groups having from 1 to 4 carbon atoms,
$R_4$ is a hydrogen atom or an alkyl group having from 1 to 4 carbon atoms, and
n is 2 or 3.

When both $R_1$ and $R_2$ are an alkyl group, the final products have the formula

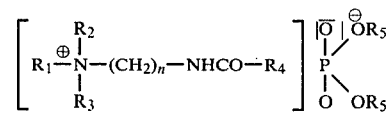

When $R_2$ is a hydrogen atom, a mixture of a compound of the above formula and a compound of the formula

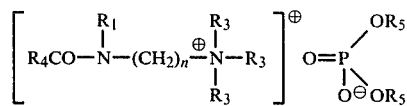

is obtained.

Both types of compounds are obtained in the synthesis in about equal amounts.

Synthesis of the amine-amide condensation products is carried out by mixing the two starting components and heating the mixture for about 2 to 6 hours at 130°–170° C. without a solvent, while distilling off the water of reaction formed. The molar ratio of the starting components is from 0.8 to 1.3 mol acid to 1 mol amine; preferably, the two components are used in equal molar amounts. Instead of the free carboxylic acid, the functional derivatives thereof may be used, such as anhydrides or chlorides. Formic and acetic acid are preferred. The subsequent quaternization is carried out in known manner (U.S. Pat. No. 2,563,506) by adding an alkali metal hydroxide and the required amount of trialkyl phosphate. The water-containing reaction product so obtained can be directly added to the fiber preparation. Alternatively, of course, the quaternized amine-amide condensation product can be purified by removing the water, or further diluted by adding more water.

Surprisingly, the quaternary ammonium compounds so obtained are transparently soluble in mineral oils and ester oils, for example butyl stearate, pentaerythritol tetrapelargonate, hexadecyl nonanate etc., and they are well compatible with the aqueous emulsions prepared from oil-containing filament preparation systems. This is especially surprising, because corresponding quaternized amines without amide groups are scarcely soluble in mineral oils. The compounds of the invention, being quaternary ammonium compounds, have a very good antistatic action and are stable to heat. The may be applied as 100% substances, as soft pastes or as liquids. With addition of small amounts of water, liquid concentrates capable of being pumped or poured can be prepared.

The products, applied in an amount of from 0.01 to 3%, preferably 0.1 to 0.6%, impart excellent antistatic properties to fibers. Especially advantageous is their use in mineral oil or ester oil filament preparation systems, where, added in an amount of from 5 to 40%, preferably 10 to 25%, they impart sufficient antistatic properties to filaments of polyamide, polyesters, polyolefins or regenerated cellulose. Used in spooling and batching oils, the products of the invention yield good antistatic values, too. They may be applied to the fibers and filaments by dipping, spraying or padding by means of godets gear pumps or immersion rollers. The products are used during the manufacture of the fibers or filaments, or their processing, for example in the form of sprayable oily lubricatns. During the manufacture of the fibers, the products may be applied in the form of spin-preparation, draw-preparatoin or final preparation, and they may be used per se or in addition to other preparation components such as nonionic oxethylates, silicon derivatives, sarcosides etc.. Suitable fibrous materials to be treated with the products of the invention are especially polyesters, polyamide, polyacrylonitrile, polyolefins, regenerated cellulose or cellulose fibers.

The following examples illustrate the invention.

EXAMPLE 1

362 g tallow propylenediamine are heated to 60° C. 46 g 98% formic acid are poured in with agitation, and the batch is heated at 150° C. for 3 hours ½ under a nitrogen blanket. 16.5 g water (acid number: 5) are distilled off. The batch is cooled to 65° C., 140 g 29% sodium hydroxide solution are added, and 280 g trimethyl phosphate are added dropwise within 60 minutes and with thorough agitation. Agitation is then continued for 2 hours ½ at 60°–70° C. About 800 g of product are obtained containing about 85% of active substance. This liquid product can be applied without further dilution. Formula:

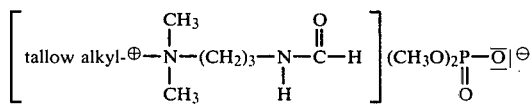

EXAMPLE 2

362 g tallow propylenediamine are heated to 60° C. 60 g glacial acetic acid are poured in with agitation, and condensation proceeds under a nitrogen blanket at 150° C. for 4 hours ½. 16 g water (acid number: 5) are distilled off. The batch is cooled to 65° C., 140 g 29% sodium hydroxide solution are added, and 280 g trimethyl phosphate are added dropwise within 60 minutes and with thorough agitation. Agitation is continued for 2 hours ½ at 60°–70° C., and 820 g of product containing about 85% of active substance are obtained. The product is liquid. Formula:

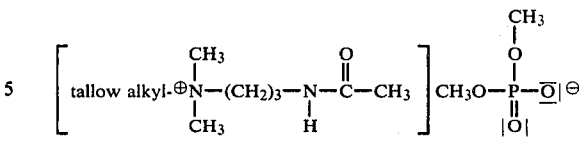

EXAMPLE 3

256 g lauryl-propylenediamine are heated to 50° C. 60 g glacial acetic acid are poured in with agitation, and the batch is heated for 6 hours at 150° C. under a nitrogen blanket. 16.5 g water (acid number: 5) are distilled off. The batch is cooled to 65° C., 140 g 29% sodium hydroxide solution are added, and 280 g trimethyl phosphate are added dropwise with thorough agitation (within 60 minutes). Agitation is continued for 2 hours ½ at 60°–70° C., and 720 g of product having a content of about 85% of active substance are obtained. The liquid product can be directly applied. Formula:

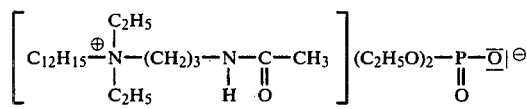

EXAMPLE 4

The following oil and ester oil preparations were prepared:
(1) mineral oil system I 50 parts mineral oil (viscosity at 20° C.: 32 cP; 62% paraffins; 38% naphthenes) 20 parts coconut fatty alcohol . 5 EO 20 parts isotridecyl alcohol . 3 EO 10 parts lauryl alcohol—4 EO—POCl₃ ester
(2) mineral oil system II according to German Pat. No. 2,326,966, Example 1a
(3) mineral oil system III according to German Offenlegungsschrift No. 25,28,734, Example I 3

| (4) | ester oil system |
|---|---|
| | 43 parts pentaerythritol-tetradecylate |
| | 57 parts emulsifier |
| Emulsifier: | 6 parts oleyl alcohol . 5 EO |
| | 1 part oleyl alcohol . 8 EO |
| | POCl₃ ester |
| | 1 part castor oil . 7.5 EO |
| | 3 parts coconut fatty acid . 8 EO |
| | 1 part H₂O |

The four oil systems were combined with the following quaternary ammonium compounds:
(a) tallow propylenediamine, perquaternized with dimethyl sulfate according to German Pat. No. 2,335,675, Example 1b (Comparison)
(b) permethylated condensation product of 1 mol diethylenetriamine and 1 mol stearic acid, according to the above German Patent, Example 1a (Comparison)
(c) According to the invention, Example 1.
(d) According to the invention, Example 2.
(e) According to the invention, Example 3.

These quaternary ammonium compounds were added to the above oil systems in amounts of 10 and 20 weight %, relative to the oil systems.

As to the compatibility of these preparation systems, the following was stated: The systems containing products (a) and (b) immediately separated into phases. The products (c) to (e) according to this invention transparently dissolved in the four oil systems. When 10% aqueous emulsions were prepared from the mineral oil and ester oil systems containing 10 to 20 weight %, respectively, of the products (c) to (e) of the invention, stable systems were obtained which did not separate into phases even after a several days standing, and part of which were transparent.

EXAMPLE 5

Thermostability test
(a) product according to Example 1 (according to invention)
(b) product according to Example 2 (according to invention)
(c) product according to Example 3 (according to invention)
(d) product according to German Pat. No. 2,335,675, Example 1a
(e) product according to U.S. Pat. No. 2,742,379, Example I (dodecanol . P$_2$O$_5$-diethanolamine salt)

The products were maintained for 1 hour at 220° C. The following losses of active substance and the following yellowings resulted:

| a: | 3.2% | ICN* | : | 20 |
|---|---|---|---|---|
| b: | 2.8% | | : | 15 |
| c: | 4.5% | | : | 10 |
| d: | 19% | | : | 1 100 |
| e: | 45% | | : | 1 100 |

*ICN: Yellowing expressed by Iodine Color Number (German Industrial Standard DIN 6112), measured subsequently to the volatility test.

EXAMPLE 6

The following antistatic tests were carried out:
(a) mineral oil system I (Example 4)+20% product according to Example 1
(b) mineral oil system I+20% product according to ample 2
(c) mineral oil system I+20% product according to Example 3
(d) mineral oil system I+20% dodecanol-P$_2$O$_5$-diethanolamine salt according to U.S. Pat. No. 2,742,379, Example I, as comparative product.

10% emulsions of these transparent systems, prepared with water, had the following aspect:
(a) to (c) (according to invention): opaque microemulsions,
(d) (comparison): milky emulsion which separated into phases after 48 hours.

These emulsions were freshly applied to PAC flocks (deposit of active substance: 0.5%) and dried at 80° C. The following antistatic values were measured (values in mega-ohms):

| | | 22° C. | |
|---|---|---|---|
| | | 65% rel. moisture | 30% rel. moisture |
| 25a: | | 20 | 40 |
| b: | | 100 | 200 |
| c: | | 4 | 20 |
| d: | (Comparison) | 250 | 10$^6$ |

What is claimed is:
1. Quaternized amine-amide condensation products obtained by condensation of an amine of the formula

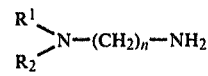

with a carboxylic acid of the formula

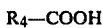

and subsequent quaternization with a trialkyl phosphate of the formula

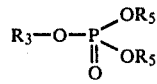

in which formulae
R$_1$ is an alkyl or alkenyl group having from 7 to 20 carbon atoms,
R$_2$ is an alkyl group having from 1 to 20 carbon atoms, or a hydrogen atom,
R$_3$ and R$_5$ are identical or different alkyl groups having from 1 to 4 carbon atoms,
R$_4$ is a hydrogen atom or an alkyl group having from 1 to 4 carbon atoms, and
n is 2 or 3.
2. Fiber preparation systems containing a quaternized amine-amide condensation product as claimed in claim 1.
3. Polyesters, polyamide, polyacrylonitrile, polyolefins, regenerated cellulose or cellulose textile fibers coated with a fiber preparation system containing a quaternized amine-amide condensation product as defined in claim 1.

* * * * *